US005512282A

United States Patent [19]
Krivan et al.

[11] Patent Number: 5,512,282
[45] Date of Patent: Apr. 30, 1996

[54] MONOSPECIFIC POLYCLONAL ANTIBODIES TO SHIGA-LIKE TOXINS

[75] Inventors: Howard C. Krivan, Bethesda; James E. Samuel, Germantown, both of Md.

[73] Assignee: MicroCarb, Inc., Gaithersburg, Md.

[21] Appl. No.: 174,294

[22] Filed: Dec. 28, 1993

Related U.S. Application Data

[63] Continuation of Ser. No. 858,299, Mar. 26, 1992, abandoned.

[51] Int. Cl.⁶ .................. A61K 39/108; A61K 39/40; C07K 16/12; G01N 33/53
[52] U.S. Cl. .................. 424/169.1; 424/164.1; 424/234.1; 424/236.1; 424/241.1; 435/7.32; 435/7.37; 530/389.5; 530/390.1
[58] Field of Search .................. 424/85.8, 92, 130.1, 424/150.1, 164.1, 167.1, 169.1, 184.1, 234.1, 236.1, 241.1; 435/7.92, 70.21, 7.1, 7.2, 7.32, 7.37, 7.92; 530/389.1, 389.5, 390.1; 436/536

[56] References Cited

U.S. PATENT DOCUMENTS

| | | |
|---|---|---|
| 3,907,987 | 9/1975 | Wilson . |
| 3,975,517 | 8/1976 | Wilson . |
| 3,984,539 | 10/1976 | Khouw et al. . |
| 4,530,833 | 7/1985 | Wilkins et al. . |
| 4,533,630 | 8/1985 | Wilkins et al. . |
| 4,816,252 | 3/1989 | Stott et al. . |
| 4,863,852 | 9/1989 | Wilkins et al. . |
| 4,879,218 | 11/1989 | Wilkins et al. . |

OTHER PUBLICATIONS

Ashkenazi et al., J. Pediatr. 113: 1008–1014, 1988.
MacLeod et al., Vet. Microbiol. 29: 309–318, 1991.
Brussow et al., 1987, *Journal of Clinical Microbiology*, 982–986.
Davidson et al., 1989, *The Lancet*, 709–712.
Archambault et al., 1988, *Am. J. Vet. Res.*, 49(7):1084–1091.
Mietens and Keinhorst, 1979, *Eur. J. Pediatr.*, 132:239–252.
Tacket et al., *The New England Journal of Medicine*, 318(19):1240–1243.
Boesman-Finkelstein, 1989, *Infection and Immunity*, 1227–1234.
Karmali, 1989, *Clinical Microbiology Reviews*, 15–38.
Samuel et al., 1990, *Infection and Immunity*, 58(3):611–618.
"Unravelling HUS", 1987, *The Lancet*, 1437–1439.
Harari et al., 1988, *Infection and Immunity*, 56:1618–1624.
Donohue-Rolff, 1989, *Infection and Immunity*, 57:3888–3893.
Boyd et al., 1991, *Infection and Immunity*, 59:750–757.

*Primary Examiner*—Margaret Parr
*Assistant Examiner*—Phillip Gambel
*Attorney, Agent, or Firm*—Pennie & Edmonds

[57] ABSTRACT

Disclosed herein are high titer, monospecific, polyclonal antibodies to Shiga-like toxins. Also disclosed are methods for producing such antibodies, compositions containing them, and methods for the diagnosis, prevention, and treatment of diseases caused by Shiga-like toxins. These include hemorrhagic colitis and hemolytic uremic syndrome in humans, edema disease in swine, and calf diarrhea in cattle.

18 Claims, 1 Drawing Sheet

MONOSPECIFIC POLYCLONAL ANTIBODIES TO SHIGA-LIKE TOXINS

This is a continuation of application Ser. No. 07/858,299, filed Mar. 26, 1992, now abandoned.

FIELD OF THE INVENTION

The present invention relates to antibodies to Shiga-like toxins. More particularly, it relates to high titer, monospecific, purified polyclonal antibodies to Shiga-like toxins and methods of preparing and using the antibodies. The invention also relates to the pharmaceutical compositions containing the antibodies and methods of preparing and using such compositions. Finally, the invention relates to reagents and kits for detecting the presence of Shiga-like toxins in a sample and to methods for using such reagents and kits. The antibodies, pharmaceutical compositions, reagents, and diagnostics kits of the invention are particularly useful for the diagnosis, prevention, and treatment of serious, often life-threatening diseases in humans and animals caused by Shiga-like toxins.

REFERENCES

Several publications, patents, and a patent application are referenced herein. The disclosures of these references are incorporated herein by reference in their entirety, unless otherwise noted.

BACKGROUND OF THE INVENTION

Shiga-like toxins (SLTs) are a family of powerful, disease-producing toxins produced by certain strains of *Escherichia coli*, a type of common bacteria found in humans and animals. SLTs derive their name from the fact that they are cytotoxins similar in both structure and function to Shiga toxin, which is a protein cytotoxin produced by *Shigella dysenteriae* type 1. This Shigella serotype is responsible for the most severe cases of bacillary dysentery. (SLTs are also known as verotoxins (VTs) because many serotypes that produce this toxin were originally characterized as being vero cell toxinogenic.) The SLT-producing *E. coli* is a heterogeneous group of bacteria that belong to several different O:H:K serotypes, but they all have in common the ability to discharge one or more SLTs.

SLT-producing *E. coli* cause a spectrum of diseases in humans from mild, uncomplicated diarrhea and bloody diarrhea to two life-threatening complications, hemorrhagic colitis and hemolytic uremic syndrome (HUS). The life-threatening conditions result from the systemic action of the toxins.

Infants, young children, and the elderly are most susceptible. HUS is a leading cause of acute renal failure in childhood. The syndrome has a fatality rate of about 10%. Up to 30% of HUS survivors develop long-term residual disability, such as chronic renal failure, hypertension, or neurological deficit. In two recent pediatric outbreaks of SLT-producing *E. coli* in North America, about 7% of symptomatic children developed HUS. In another outbreak in a nursing home in the United States, HUS occurred in 24% of residents, most of whom died. The organism is also showing up in school lunches and, according to the USDA Food Safety and Inspection Service, is a major problem of serious concern. Although information on the incidence of infection is limited, SLT-producing *E. coli* was recently found to rival Salmonella and Campylobacter as the most common cause of bacterial diarrhea. Karmali, *Clin. Microbiol. Rev.* 2:15–38 (1989).

Foods of animal origin are the major source of human infection. Although infants, young children, and the elderly are most susceptible, anyone who eats contaminated food can become infected. Infection may also be acquired by person-to-person transmission, which is especially a problem in day care centers and nursing homes.

At least two serologically distinct bacteriophage-mediated SLTs, SLT-I and SLT-II, are involved in human disease. Human isolates of SLT-producing *E. coli* (SLTEC) elaborate various amounts of either one or both SLT-I and SLT-II. SLT-I is nearly identical, structurally and antigenically, to Shiga toxin. Shiga toxin, SLT-I, and SLT-II are all subunit toxins composed of an enzymatically active A subunit and a number of B subunits that allow binding of the toxin to a specific eucaryotic cell receptor. The toxins kill the cells by inactivating the 60S ribosomal subunit. Binding is followed by internalization of the A subunit, where it inhibits protein synthesis in mammalian cells by inactivating 60S ribosomal subunits through selective structural modification of 28 S ribosomal RNA.

Although SLT-I and SLT-II have a similar subunit structure, bind to the same glycolipid receptor, and inhibit protein synthesis by the same mechanism as Shiga toxin, they also show differences in biological activities in tissue culture and animal models. They also fail to cross-neutralize.

SLT-producing *E. coli* also causes edema disease (ED) in swine. This disease is a usually fatal condition of weanling pigs, characterized by anorexia, edema of the eyelids, and neurological abnormalities consisting of incoordination and paralysis. *E. coli* isolates from swine with ED produce an SLT-II related toxin, designated SLT-IIv or VTE. SLT-IIv from edema disease strains differs from SLT-I and SLT-II in that it is much less active on HeLa cells, but very active on Y-1 adrenal cells and Vero cells. The cytotoxicity of SLT-IIv can be neutralized by antiserum to SLT-II. Marques, et al., *FEBS Microbiol. Lett.* 44:33–38 (1987).

Antibiotics are contraindicated in the treatment of SLT-producing *E. coli* infection in humans and pigs. Antibiotics actually enhance toxin production by the bacteria. Therefore, their use increases the risk of developing complications such as HUS. To date, treatment of SLTEC infection relies solely on the optimal management of the physiological complications of the infection, i.e., fluid and electrolyte imbalances, anemia, renal failure, and hypertension. Other than that, there is no effective therapy or prevention regimen for the possible development of HUS. Similarly, there is no effective therapy or prevention for swine edema disease.

The only way to control human infection is to address the animal reservoirs. This means instituting practices at the abattoirs and processing plants to reduce cross-contamination between food products from different sources. The USDA and the meat packing industry are thus particularly in need of a rapid test for detecting SLT-producing bacteria.

At present, the toxins are detected by a tedious and time consuming (but highly sensitive) procedure involving the determination of cytotoxicity to cells in culture. The cytotoxicity assay is therefore performed in only a very few centers around the world, mainly reference and research laboratories. Test results take several days to be received.

Moreover, clinical microbiology laboratories and reference laboratories (including the Center for Disease Control and the U.S. Department of Agriculture) rely on the isolation of only a single serotype, 0157:H7, largely because the organism has a phenotypic property (sorbitol negative after 24 h) that facilitates detection from fecal filtrates or mixed flora. However, there are over 50 serotypes of SLT-producing *E. coli* . Approximately 33 million human fecal samples are tested annually by clinical microbiology labs for pathogens in this country, and an additional 50–100,000 meat samples are tested by the USDA. Therefore, an overall diagnostic strategy, directed toward quickly and effectively detecting the toxin rather than detecting a single serotype, is needed.

A major defense mechanism of humans and animals against pathogenic organisms, such as SLT-producing *E. coli*, is their ability to produce antibodies that bind to the pathogens and their toxins, inactivating them or preparing them for destruction by specialized cells in the body. Scientists have taken advantage of this fact by inoculating large mammals, such as horses and cows, with various pathogens, toxins, and other antigens, relying on the animal's immune system to produce large quantities of antibodies to the inoculated material. The antibodies are recovered from the animals and then used to treat infections in humans and animals caused by the pathogen or to passively immunize humans and other animals against the pathogen. Such antibodies are also used in immunoassays for the detection of toxins and pathogenic organisms.

Passive immunization also occurs naturally. Humans and many types of animals are born lacking antibodies. They receive some protection by ingesting colostrum and milk from their mother. The colostrum and milk contain appreciable quantities of antibodies and thus are a form of passive immunization.

Cows secrete large amounts of IgG1 immunoglobulin in colostrum and milk. These bovine IgG1 antibodies are relatively protease-resistant and highly homologous with human immunoglobulin G. See, e.g., Lascelles, et al., *Transplant. Rev.* 19:170–208 (1974) and McLead, et al. *Infect. Immun.* 44:474–478 (1984).

Several investigators have examined the possibility of using bovine colostrum and milk for passive immunization or treatment of certain diseases in humans and animals. However, the diseases were not caused by SLT-producing *E. coli*. The inventors are unaware of any attempts to immunize cows with SLTs to produce milk that contains anti-SLT immunoglobulins.

In 1979, Mietens et al. treated 60 infants with acute *E. coli* gastroenteritis with a bovine milk immunoglobulin concentrate containing antibodies to enteropathogenic strains of *E. coli* . The concentrate was obtained by hyperimmunization of pregnant cows with the 14 *E. coli* serotypes that are most frequently responsible for infantile gastroenteritis. Milk obtained during the first 6–8 days of lactation was collected. After skimming, the casein was removed by acid precipitation at pH 4.6 and subsequent centrifugation. The bulk of the lactose and mineral salts was removed by exhaustive ultra- and diafiltration in a reverse osmosis system. The whey protein solution was sterilized by filtration and dried by lyophilization to produce the immunoglobulin concentrate. The results of the study provided evidence that treatment with the milk immunoglobulin concentrate was effective in eliminating enteropathogenic *E. coli* from the intestine. Mietens, et al., *Eur. J. Pediatr.* 132:239–252 (1979).

Tacket et al. reported a double-blind, controlled study in which a bovine milk immunoglobulin concentrate with high titers of antibodies against enterotoxigenic *E. coli* was used as prophylaxis against *E. coli* challenge in 10 adult volunteers. Lyophilized milk immunoglobulins were prepared from the colostrum of cows immunized with several enterotoxigenic *E. coli* serotypes, *E. coli* heat-labile enterotoxin, and cholera toxin. Ten volunteers received the concentrate, and 10 others received a different immunoglobulin concentrate with no anti-*E. coli* activity. After challenge with enterotoxigenic *E. coli*, 9 of the 10 controls had diarrhea, but none of the 10 persons who had received the immunoglobulin concentrate against *E. coli* had diarrhea. Tacket et al., *N. Engl. J. Med.* 318:1240–1243 (1988).

Several investigators examined the use of bovine milk immunoglobulins for passive immunization against rotavirus infection. Brussow et al. hyperimmunized pregnant cows with four human rotavirus serotypes, resulting in a 100-fold increase in neutralizing milk antibody titers over those of controls. The prepared milk immunoglobulin concentrate consisted of 50% bovine milk immunoglobulins and showed neutralizing activities against the four rotavirus serotypes that were 100 times higher than those in pooled human milk samples and 10 times higher than those in a commercial pooled immunoglobulin preparation from whole human blood serum. The authors proposed that the concentrate be used to induce passive immunity to infantile rotavirus gastroenteritis. Brussow et al., *J. Clin. Microbiol.* 25:982–986 (1987). Davidson et al. produced a bovine colostrum with a high antibody titer against the four known human rotavirus serotypes and found that it protected susceptible children against rotavirus infection. Davidson et al., *The Lancet* (Sep. 23, 1989), pgs. 709–712. Archambault et al. inoculated pregnant cows with a bovine rotavirus vaccine and found that the cell-free colostrum isolated from the cows protected newborn calves from a rotavirus challenge exposure on the third day after birth, when they were fed the supplement for the first five days after birth. Archambault et al., *Am. J. Vet. Res.* 49:1084–1091 (1988).

Boseman-Finkelstein et al. immunized pregnant cows with cholera toxin (CT), a CT-related enterotoxin from *E. coli*, and *Vibrio cholera* outer membranes (OMs). Purified colostral immunoglobulin was recovered and examined by various assays. Immunoglobulin preparations were administered orally in infant feeding formula to 6-day old rabbits. Anti-CT and anti-OM immunoglobulins protected against diarrhea in rabbits challenged intraintestionally by virulent cholera vibrios. The protective effects observed were primarily manifested as a delay in the onset of diarrhea disease. Boseman-Finkelstein et al., *Infect. Immun.* 57:1227–1234 (1989).

U.S. Pat. No. 3,907,987, issued Sep. 23, 1975 to Wilson, discloses the use of a live bacterial vaccine from selected strains of *E. coli* to vaccinate sows, recover the milk, and feed the milk to newborn pigs to protect against the occurrence of enteric colibacillosis. Essentially the same disclosure is contained in U.S. Pat. No. 3,975,517, issued Aug. 17, 1976 to Wilson.

U.S. Pat. No. 4,816,252 issued Mar. 28, 1989 to Stott et al., discloses a product and process for transferring passive immunity to newborn domestic animals. Immunologically active immunoglobulins are extracted from whey by-product of dairy manufacturing by using ultra-filtration techniques. The patent states that ion exchange techniques can also be used to increase the immunoglobulin concentration in the product. It further states that the dry filtered product can be fed to newborn animals to achieve passive immunity.

The use of antibodies in immunoassays is well known. This includes the use of certain monospecific antibodies. U.S. Pat. No. 4,530,833, issued Jul. 23, 1985 to Wilkins et al. and U.S. Pat. No. 4,533,630 issued Aug. 6, 1985 to Wilkins et al. disclose monospecific antibodies to each of toxin A and toxin B of *C. difficile*, purification of the antibodies, and their use in assays for *C. difficile*.

The use of certain receptors for toxins or microorganisms in assays to detect the toxins or microorganisms is also known. For example, U.S. Pat. No. 4,863,852, issued Sep. 5, 1989 to Wilkins et al., discloses the use of a particular carbohydrate structure, which is a receptor for toxin A of *C. difficile*, to detect toxin A. A specimen is contacted with a reagent containing the receptor, and an assay is conducted to determine if the toxin A is bound to the reagent. The methods for assaying for that binding include the various immunoassays, such as ELISA.

Certain receptors are known for some SLTs. Lingwood et al., *J. Biol. Chem.*, 262:8834–8839 (1987) discloses the binding of verotoxin (SLT) to globotriosyl ceramide ($Gb_3$) containing the carbohydrate sequence galactose(alpha1-4)galactose(beta1-4)glucose(beta1-1)ceramide. Samuel et al., *Infection and Immunity*, 58:611– 618 (1990) discloses the binding of SLT-I and SLT-II to Gal(alpha1-4)Gal(beta1-4)Glc(beta1-1)Cer ($Gb_3$). It further discloses that SLT-IIvp (a SLT-II-related variant produced by a porcine isolate) bound to $Gb_3$, Gal(alpha1-4)Gal(beta1-4)Glc-bovine serum albumin, GalNAc(beta1-3)Gal(alpha1-4)Gal(beta1-4)Glc(beta1-1)Cer ($Gb_4$), and Gal(beta1-3)GalNAc(beta1-3)Gal(alpha1-4)Gal(beta1-4)Glc(beta1-1)Cer ($Gb_5$). It also discloses that SLT-IIvh (a SLT-II-related variant produced by a human isolate) bound to Gal(alpha1-4)Gal-bovine serum albumin, Gal(alpha1-4)Gal(beta1-4)Glc-bovine serum albumin, Gal(alpha1-4)Gal(beta1-1)Cer ($Gb_2$), and $Gb_3$. DeGrandis et al., *J. Biol. Chem.*, 264:12520–12525 (1989) discloses that SLT-IIvp binds to $Gb_4$ and less so to $Gb_3$. Basta et al., *J. Clin. Microbiol.*, 27:1617–1622 (1989) discloses a sensitive, receptor-specified, enzyme-linked immunosorbent assay (RELISA) to detect SLT-I. $GB_3$ was de-N-acylated to yield lyso-Gb3, which was more polar but retained SLT-I binding. Lyso-$Gb_3$ was used to sensitize microdilution plates to bind SLT-I for subsequent immunodetection. The RELISA was used to detect SLT-I in the culture supernatant of a variety of bacteria of known SLT-I status. U.S. patent application Ser. No. 07/211,289 of Lingwood et al., filed Jun. 24, 1988, also discloses SLT receptors and their use in receptor-based binding assays for the detection and quantitation of SLTs.

We have discovered that pregnant cows immunized with purified SLTs produce monospecific, polyclonal antibodies to SLTs that are of a surprisingly and unexpectedly high titer. As a result, we were able to produce very high titer colostrum and milk for use in passive immunization or treatment of SLT toxemia. We also discovered that we were able to immunize the cows with active toxin without ill effect, in contrast to the usual situation in producing polyclonal antibodies where it is necessary to immunize the animal with inactive toxin. This produces antibodies that recognize native epitopes that would not be recognized if inactive toxin were used. As a result of this increased polyvalency, we were able to produce purified IgG that provides outstanding results in terms of increased signal to noise ratio when used as a reagent in assays for the detection of SLTs. The IgG was further purified to provide the monospecific anti-SLT polyclonal antibodies in pure form for use in therapeutic and other special applications. Thus, it is now possible for the first time to rapidly detect the presence of SLTs in samples and to administer anti-SLT antibodies to humans and animals for prophylactic and therapeutic purposes.

SUMMARY OF THE INVENTION

It is an object of the invention to provide SLT antitoxin and purified polyclonal antibodies to Shiga-like toxins.

Another object of the invention is to provide methods for producing the antitoxin and the purified antibodies.

A further object of the invention is to provide pharmaceutical compositions for the prevention, amelioration, or treatment of disease in a human or animal caused by an SLT together with methods of using such compositions.

Yet another object of the invention is to provide methods, reagents, and kits for the detection or other investigational analysis of SLTs.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

To achieve the objects and accordance with the purpose of the invention, as embodied and broadly described herein, the present invention provides an antitoxin to one or more SLTs. It comprises purified IgG that contains high titer, monospecific polyclonal antibodies to a Shiga-like toxin.

The antibodies can be purified from the IgG. Therefore, the invention also provides high titer, monospecific, purified polyclonal antibodies to an SLT. Preferably, the antibodies comprise bovine IgG.

In another embodiment, the invention comprises a method for producing the purified IgG. An animal that tolerates purified, active SLT is inoculated with a purified SLT. After the animal has had an immune response to the toxin, purified IgG is recovered from the animal. Preferably, the animal is a cow and most preferably a pregnant cow.

Preferably, the purified IgG is further purified by affinity chromatography, using the purified SLT. This produces the high titer, monospecific, purified polyclonal antibodies of the invention.

The invention further comprises methods and pharmaceutical compositions for the prevention, amelioration, or treatment of disease in a human or animal caused by an SLT or by bacteria that produce an SLT. A therapeutically or prophylactically effective amount of the purified IgG or the purified antibodies of the invention are administered to the human or animal host. Preferably, they are administered in a pharmaceutically acceptable carrier.

In a preferred embodiment of the invention, the carrier is bovine colostrum or milk that contains the antibodies. Such a composition is preferably prepared by inoculating a pregnant cow with a purified, active SLT and milking the cow after it has an immune response to the antigen, thereby obtaining first the colostrum and then the milk.

The invention further comprises methods for detecting the presence or concentration of an SLT, or the presence of SLT-producing bacteria, in a sample suspected of containing such an SLT or bacteria. The sample is contacted with the purified IgG or the antibodies of the invention, and a determination is made whether or not an antibody-antigen reaction has occurred. Preferably, the IgG or antibodies are used in an ELISA, and most preferably used in a receptor-based ELISA. In an alternative preferred embodiment, the IgG or antibodies are attached to solid particles, such as latex beads, and the presence of the SLT is detected by the agglutination of the solid particles.

The invention also provides reagents and kits. The reagents comprise the purified IgG or the antibodies in a liquid or attached to a substrate, such as an insoluble solid support. Preferably the solid support is the well of a microtiter plate or solid particles, such as latex beads. The diagnostic kit comprises the reagents of the invention and a way of detecting or measuring the complexes created by the binding of the SLT with the IgG or antibodies in the reagent. Preferably, the detecting or measuring means is a reagent which is capable of binding to the complexes formed by the SLT and the IgG or antibodies and which contains a detectable moiety. Preferably, the reagent is a receptor that binds to the SLT.

In the most preferred embodiment, the diagnostic kit comprises, in a container, an SLT receptor attached to a solid support and the purified IgG of the invention. Preferably, the solid support is the well of a microtiter plate. Preferably, the kit also contains a means for detecting the binding of the anti-SLT antibodies in the purified IgG to SLT that has bound to the receptor.

The accompanying drawings, which are incorporated in and constitute a part of this specification, illustrate one embodiment of the invention and, together with the description, serve to explain the principles of the invention.

DETAILED DESCRIPTION OF THE INVENTION

Figure 1:
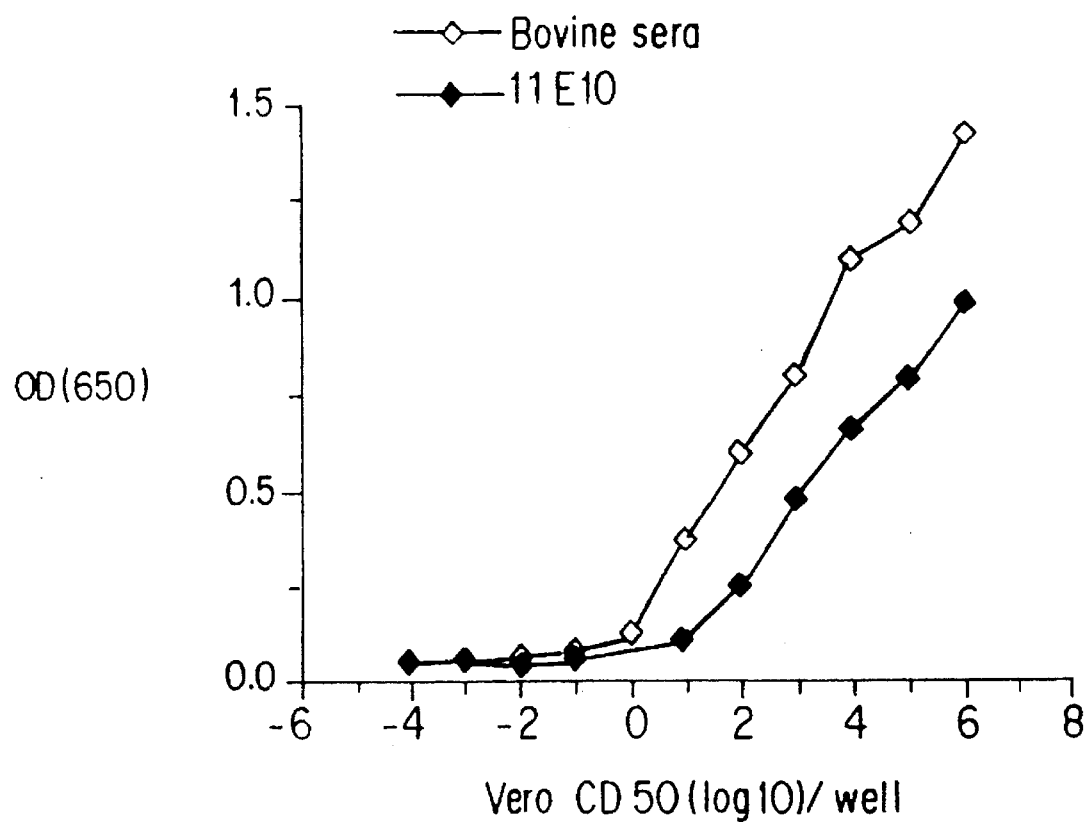
FIG. 1 shows bovine polyclonal antibody compared to monoclonal antibody 11E10 for detecting toxin bound in the RELISA. Purified IgG from bovine source or from a hybridoma culture was used at 10 ug/ml to detect 10-fold dilutions of purified SLT-II bound to the receptor analogue lyso-Gb3 in 96-well microtiter plates. The RELISA was developed with horseradish peroxidase conjugated secondary antibody and TMB substrate.

Reference will now be made in detail to the presently preferred embodiments of the invention, which, together with the following examples, serve to explain the principles of the invention.

The present invention provides purified IgG comprising high titer, monospecific polyclonal antibodies to SLTs. Preferably, the IgG is bovine IgG.

As used herein, the term "purified IgG" refers to IgG that is essentially free of proteins that are not immunoglobulin G, as understood by persons skilled in the art. The purity of the IgG of the invention is shown by the fact that it produces only two bands when run on SDS-PAGE and stained with both silver and coomassie blue. The bands are at about 47 kDa and 30 kDa, and they represent the heavy and light chains of the IgG.

As used herein, the term "monospecific" refers to antibodies that do not have any epitopes for antigens other than SLTs. The monospecificity of the antibodies of the invention are shown by the fact that when lysates of SLT-producing *E. coli* are run on a Western blot, they react specifically with the toxin to form bands.

As used herein, the term "high titer" refers to a purified IgG composition wherein the antibodies in the composition have an average neutralizing titer of at least 1:250,000/mg IgG as measured by toxin neutralization of vero cells and an average toxin-reactive antibody titer of at least 1:12000/mg IgG as measured by enzyme-linked immunosorbant assay (ELISA).

As used herein, the term "Shiga-like toxin (SLT)" refers to any cytotoxin similar in both structure and function to Shiga toxin. Known SLTs include SLT-I, SLT-II, and SLT-III. They also include known variants of SLT-II, which are SLT-IIv, SLT-IIvh, and SLT-IIvp. The term encompasses the presently unknown SLTs or variants thereof that may be discovered in the future, since their characterization as an SLT or variant thereof will be readily determinable by persons skilled in the art.

The purified IgG of the invention is made by a novel modification of standard techniques for making polyclonal antibodies by inoculating an animal with an antigen and recovering immunoglobulins from a fluid, such as serum, that contains the immunoglobulins after the animal has had an immune response. The inventors surprisingly and unexpectedly discovered that they were able to inoculate a bovine animal with a purified, preferably active, SLT without significant ill effect to the animal.

Without wishing to be bound by theory, the inventors hypothesized that the cell membranes of the cells of such an animal do not contain a receptor for SLTs or only contain low levels of receptors, when compared to other mammals or humans. Presumably, this allows high amounts of purified, active toxin to be inoculated into the animal and presumably allows the toxin to remain in unbound form longer in the animal, thereby creating a much greater antigenic response.

Therefore, the method of the invention is applied to any animal that has few or no receptors to SLTs. Such animals can be identified by those skilled in the art through standard techniques involving the injection of an SLT into the animal and the observation of its effect on the animal and the titer of antibodies produced by the animal.

Cattle are the preferred animals. Pregnant cows are most preferred because they produce higher levels to antigens when they are pregnant and the antibodies can be recovered from the colostrum or milk (hereinafter collectively called "milk").

Alternatively, the purified IgG can be obtained from serum. Pregnant or non-pregnant cows or even bulls may be used to provide the serum. This method is generally more preferred because the IgG is more easily recovered from serum than milk. Pregnant cows are still most preferred because of their greater level of antibody production.

The SLT is purified and prepared for inoculating by known techniques. Preferably, the antigen is emulsified, using a biologically suitable emulsifying agent, such as Freunds incomplete adjuvant. The antigen may also be immobulized onto a bead and/or linked to an immunogen prior to administration. In this manner, the animal's system is prevented from quickly clearing the toxin, thereby enhancing production of the antibodies. A single type of SLT, such as SLT-II, or a variant thereof, such as SLT-IIvp, can be injected. This provides polyclonal antibodies that are monospecific to just that type of SLT or variant.

The methodology need not be limited to the use of a single type or variant of SLT. A mixture of purified SLTs can be inoculated into the animal. This eventually provides polyclonal antibodies that are monospecific to the different SLTs that were used. Monospecific antibodies to particular SLTs could also be mixed together to achieve the same effect. In addition, a subunit of one or more of the toxins can be used.

While active toxin is preferred, partially or completely inactivated toxin may also be used. These can be prepared by a variety of methods, including, for example, site-specific mutagenesis, heat inactivation, or chemical inactivation.

Dairy cows will normally be used, particularly those breeds giving the highest yield of milk, such as the Holstein-Frisian and German Brown breeds. Preferably, the pregnant cow is first inoculated starting in the third trimester of pregnancy and not later than the third or fourth week pre-parturation. After the initial inoculation, the cow is boosted with additional doses on a periodic basis prior to calving and ending about two days after calving.

In a preferred embodiment, a moderate dosage of about 1–10 ml of emulsified toxin 1:1 (volume/volume) Fruends incomplete adjuvant and SLT is administered weekly during the last ten to twelve weeks of pregnancy. The antigen may be administered intramuscularly in each of the four quadrants of the cow, via intramuscular injection deep into the cow's hip, or by intravenous injection. The toxin may also be administered subcutaneously, preferably near the lymph nodes, directly into the retromammary lymph nodes, or intra-cycternally through the teat channels. The preferred mode of inoculation is by intramuscular injection. Pre-and post-administration blood samples may be taken to monitor the cow's serological response.

At birth, the calves are separated and hand-reared. The cows are milked after calving to obtain colostrum and milk containing antibodies reactive with SLT, and the milk is stored frozen until processed. The inoculated pregnant cow secretes large quantities (about 1 kg of IgG1 per colostrum and about 0.1 to 0.5 kg of IgG1 per liter milk) of antibody. Cows immunized with higher dosages of SLT antigen exhibit higher antitoxin titers in colostrum than cows immunized with lower dosages.

The purified IgG is recovered from the milk or serum of the animal by standard techniques as applied by the teachings contained herein. For pregnant cows, the techniques include those disclosed in U.S. Pat. No. 3,984,539 issued Oct. 5, 1976 to Khouw et al. and U.S. Pat. No. 4,816,252 issued Mar. 28, 1989 to Stott et al. Briefly, the colostrum and/or milk is obtained, and the cream is removed. The casein is removed from the skim colostrum/milk to produce whey. A suitable casein-precipitating substance, such as commercially available rennet, is used to precipitate the casein. The immunoglobulins are removed from the whey, and the purified IgG is recovered from the immunoglobulins. The milk products may be centrifuged, and may undergo pasteurization, separation, clarification, diafiltration and may be further processed by sterile filtration through a membrane filter and, before freeze-drying, if desired, the resulting sterile milk immunoglobulin concentrate solution may be further reduced by evaporation.

Preferably, the purified IgG is recovered by using affinity chromatography, wherein protein A, which binds to IgG, is bound to a chromatographic support. The immunoglobulins are contacted with a protein A bound to a solid support for a sufficient time and under appropriate reaction conditions to bind the IgG to the protein A. The time and reaction conditions will be readily determinable by those skilled in the art, given the teachings contained herein. Unbound immunoglobulins are removed, and the IgG is removed from the bound protein A by known techniques, thereby recovering the IgG in purified form, i.e., essentially free to proteins that are not IgG.

Alternatively, the purified IgG is recovered from bovine serum by standard techniques. Briefly, the proteins are precipitated by adding a salt, preferably ammonium sulfate. The precipitate is resuspended in a solvent, preferably saline, and the salt is removed from the suspension by dialysis. The IgG is recovered from the dialysate by affinity chromatography, using Protein A or Protein G.

The purified IgG obtained by this methodology will be very high titer and contain monospecific, purified polyclonal antibodies reactive with the SLT used to inoculate the animal. Despite its very high titer, the composition will contain some IgG that is not reactive with any SLT. Such IgG will be the result of immune reactions to various antigens to which the animal had been exposed throughout its life.

For certain applications, particularly certain pharmaceutical applications, it is preferable to obtain a composition wherein the IgG is essentially free of IgG that does not react with the SLT. This composition is composed virtually entirely of the high titer, monospecific, purified polyclonal antibodies to one or more SLTs.

Such antibodies are prepared by affinity chromatography, using the purified SLT bound to a chromatographic support. Purification of antibodies by affinity chromatography is generally known to those skilled in the art. See, for example, U.S. Pat. No. 4,533,630 issued Aug. 6, 1985 to Wilkins et al. Briefly, the purified IgG is contacted with the purified SLT bound to a solid support for a sufficient time and under appropriate conditions to bind that IgG which reacts with the SLT to the SLT. Such time and conditions will be readily determinable by those skilled in the art from the teachings herein. The unbound, unreacted IgG is then removed, such as by washing. The bound IgG is then recovered from the SLT by removing it through known techniques. This produces the purified, monospecific polyclonal antibodies of the invention.

The purified IgG and purified antibodies of the invention have various therapeutic, diagnostic, and scientific applications. One important application is for treating, preventing, or ameliorating illness or infection in a human or animal host caused by SLTs. A human or animal may be passively immunized against SLT toxemia or against SLTEC by administering a prophylactically effective amount of the IgG or the antibodies of the invention to the human or animal. Such passive immunization is generally done prior to the onset of disease or in the very early stages of the disease. At later stages, a therapeutically effective amount of the IgG or antibodies, which amount will generally be higher than that required for prophylaxis, is administered to the host. A therapeutically effective amount would be that amount for treating or ameliorating the infection.

The host or patient is preferably a mammal and most preferably a human or a pig. The primary diseases to be targeted are bloody diarrhea, hemorrhagic colitis, and hemolytic uremic syndrome in humans, swine edema disease in pigs, and calf diarrhea in cattle.

The actual amount of IgG or antibodies to be administered for a prophylactic or therapeutic effect will depend upon the particular disorder being treated and the size and/or age of the human or animal. Such dosages will be readily determinable by those of ordinary skill in the art, given the teachings contained herein. The usual dose range would be 100 mg to 5 gm of immunoglobulin.

Generally, the IgG or antibodies are administered in a pharmaceutically acceptable or compatible carrier. Accordingly, the invention encompasses a pharmaceutical composition for the prevention, amerlioration, or treatment of disease in a human or animal caused by SLT or by bacteria that produce an SLT. The composition comprises, in a carrier, an effective amount of the IgG or antibodies of the invention for such prevention, amerlioration, or treatment. The IgG or antibodies may be an admixture with the carrier or bound to it.

The compositions are prepared by techniques known in the art, given the teachings contained herein. The IgG or antibodies are mixed with additives customary for pharmaceutical purposes, such as vehicles, stabilizers, solubilizers, or inert diluents, and converted by customary methods to a suitable administration form, such as tablets, capsules, solutions, suspensions, or emulsions. It IgG or antibodies of the invention may also be mixed with food.

The IgG or antibodies may be coupled to a macromolecular carrier, such as a natural or synthetic polymer. Preferably, such polymer is a polypeptide, such as bovine serum albumin, or a polysaccharide.

The IgG or antibodies may be incorporated into liposomes. The liposomes are preferably prepared according to the techniques of Gruner et al., *Biochemistry* 24:2833–2942 (1985).

The pharmaceutical preparations of the invention are administered locally, as by injection or topical application, intravenously, orally, intradermally, subcutaneously, intraoccularly, subconjunctively, intramuscularly, and intrathecally. The mode of administration will necessarily depend upon the disease and host involved.

In a particularly preferred embodiment, the carrier is milk (colostrum or milk). This is particularly preferred for children or infant pigs. Preferably, the milk has an average neutralizing titer of at least 1:100,000. The milk is that obtained from pregnant cows after immunization with one or more purified SLTs. No special preparation is required other than pasteurization. Preferably, the concentration of the polyclonal antibodies in the milk is increased by removing the cream and the casein as previously discussed. It is preferred that the milk immunoglobulin is concentrated to 1–10 mg/ml prior to administering to a mammal in need of such treatment. An effective amount of milk is readily determinable by persons skilled in the art, given the teachings contained herein. Such determinations will take account of the titer of the particular milk composition, the disease, and the nature of the particular patient, i.e., animal or human, age, weight, etc.

The IgG and antibodies of the invention are also useful for detecting the presence of one or more SLTs or SLT-producing bacteria in a sample suspected of containing such toxins or bacteria. The IgG or antibodies are contacted with the sample for a period of time and under assay conditions sufficient for antibodies to bind to the toxins if present. Such time and conditions can be readily determined by persons skilled in the art, given the teachings described herein. One then determines if the antibodies have bound to the toxins, forming antibody/toxin complexes. The binding of the toxins to the antibodies is determined by techniques known to those skilled in the art in conjunction with the teachings disclosed herein. This methodology can also be adapted by standard techniques to measuring the amount or concentration of the SLT in the sample.

The IgG or antibodies may be coupled to an insoluble or soluble substrate. Soluble substrates include proteins, such as bovine serum albumin.

Preferably, the antibodies are bound to an insoluble substrate, i.e., a solid support. The antibodies should be bound to the support in an amount and manner that allows sufficient binding of the toxins for detection. The actual concentration of the antibodies to a given substrate will depend upon the particular SLT to be detected, the particular antibody being used, the particular substrate, and the binding efficiency of the antibody to the toxin. The antibodies may be bound to the substrate in any suitable manner. Covalent, noncovalent, or ionic binding may be used. Covalent bonding can be accomplished by attaching the antibodies to reactive groups on the substrate directly or through a chemical linker.

The solid support may be any insoluble material to which the antibodies can be bound and which may be conveniently used in the assay of the invention. Such substrates include permeable and semipermeable membranes, glass beads, plastic beads, latex beads, plastic microtiter wells, agarose, dextran, sepharose, and diatomaceous earth. Alternatively, the antibodies may be bound to any porous or liquid permeable material, such as a screen or net. A binder may be used as long as it does not interfere with the ability of the antibodies to bind the toxins.

After the sample has been contacted with the substrate containing the antibodies for a sufficient period of time to allow the toxins to bind to the antibodies, such binding is detected through the application of the appropriate detecting means. Basically, the substrate containing the antibodies and suspected of containing toxins bound to the antibodies is contacted with a material that binds specifically to the toxins sought to be detected. Generally, the substrate is washed to remove all or substantially all unbound materials. The detecting assay may be an immunoassay, agglutination assay, thin layer chromatography assay, or cytotoxicity assay. Immunoassays include radioimmunoassays, enzyme-linked immunosorbent assays (ELISA), Western blot, immunofluorescent assays, chemiluminescent assays, and bioluminescent assays. Agglutination assays include liposome agglutination assays and latex agglutination assays. The degree or amount of binding can also be determined through the application of known techniques, providing a measurement of the amount or concentration of the SLT in the sample.

For example, a second anti-SLT antibody or a carbohydrate receptor for the SLT is brought into contact with the substrate so that, if any antibody-SLT complexes have been formed, the second antibody or receptor will bind to them. This will form IgG-SLT-second antibody complexes or IgG-SLT-receptor complexes. The second antibody or receptor are preferably labeled with a substances that is easily detected. Such detectable moieties include an enzyme or a radioactive, fluorescent, or chemiluminescent entity. The bound complexes are preferably washed to remove any unbound second antibodies or receptors, and the detectable moieties are detected.

The various detectable moieties that can be used to label the materials used in such assays, the techniques for doing so, and the various specific assays and conditions for using them are well-known to those skilled in the art. For example, see U.S. Pat. No. 4,486,530 to David et al., issued Dec. 4, 1984, U.S. Pat. No. 4,708,818 to Montagnier et al., issued Nov. 24, 1987, U.S. Pat. No. 4,753,873 to Beltz et al., issued Jun. 28, 1988, U.S. Pat. No. 4,533,630, issued Aug. 6, 1985 to Wilkins et al., and U.S. Pat. No. 4,711,955 issued Dec. 8, 1987 to Ward et al.

Various types of samples can be tested for the presence of SLTs in accordance with the invention. The sample may be a biological sample, comprising or derived from a bodily fluid or tissue extract from a human or animal patient. The sample will normally be diluted with an appropriate solution, such as physiological saline. Alternatively, a cotton swab or other material can be used to collect the toxins. The swab is then placed in a sterile solution in order to release the toxins into the solution. The solution is then tested in accordance with the invention.

The invention may also be used to test for the presence of SLTs in environments that should be sterile, such as food manufacturing facilities. Samples can be collected and prepared for analysis by various means known to those skilled in the art.

In a particularly preferred embodiment, the purified IgG or purified antibodies of the invention are bound to solid particles, and the presence of the SLT is detected by the agglutination of the solid particles. For example, the antibodies are mixed with a suspension of latex particles and bovine serum albumin to form sensitized latex particles. The sensitized particles are then contacted with a sample on a dark glass plate or slide. Agglutination indicates the presence of toxin in the sample.

In the most preferred embodiment of the diagnostic aspect of this invention, the purified IgG is used in a RELISA. This a receptor-based ELISA assay as disclosed in U.S. Pat. No. 4,863,852, issued Sep. 5, 1989 to Wilkins, et al. and in U.S. patent application Ser. No. 07/221,289 filed Jun. 24, 1988 for Verocytotoxin Receptor Assay by Lingwood, et al. Briefly, a receptor for an SLT is contacted with a sample suspected of containing the SLT, and an assay is conducted to determine if the receptor has bound to the SLT. The purified IgG is used in such assay. The purified antibodies of the invention may also be used, although this additional purity generally is not necessary.

More particularly, the RELISA involves contacting the sample with the receptor for a period of time and under assay reaction conditions sufficient for the receptor to bind to the SLT, if the SLT is present in the sample. Any receptor-SLT complexes formed are then contacted with the purified IgG of the invention for a sufficient period of time and under assay conditions sufficient for the anti-SLT antibodies in the IgG to bind to the receptor-SLT complexes. The time and other assay conditions will be readily determinable by persons skilled in the art, given the teachings contained herein. Thus, receptor-SLT-antibodies complexes are formed. The presence or absence of these complexes are detected by the application of standard techniques as modified by persons skilled in the art, once given the teachings contained herein. The techniques include radioimmunoassay, ELISA, immunofluorescence assay, latex agglutination assay, liposome agglutination assay, cell-binding cytotoxicity assay, and thin layer chromatography assay.

Preferably, the receptor is attached to the surface of a solid support. The receptor-containing solid support is brought into contact with the sample so that any SLTs in the sample will bind to the receptors, thereby forming the receptor-SLT complexes, which will be bound to the surface of the solid support. Such complexes are detected as discussed above.

The receptors are bound to the solid support in an amount and manner that allows sufficient binding of the toxins for detection. The actual concentration of the receptors to the given substrate will depend upon the particular SLT to be detected, the particular receptor being used, the particular substrate, and the binding efficiency of the receptor to the toxin. The receptors may be bound to the substrate in any suitable manner. Covalent, non-covalent, or ionic binding may be used. Covalent bonding can be accomplished by attaching the receptors to reactive groups on the substrate directly or through a chemical linker.

The solid support may be any insoluble material to which the receptors can be bound and which may be conveniently used in the assay of the invention. Such substrates include permeable and semi-permeable membranes, glass beads, plastic beads, latex beads, plastic microtiter wells, agarose, dextran, sepharose, and diatomaceous earth. Alternatively, the receptors may be bound to any porous or liquid permeable material, such as a screen or net. A binder may be used as long as it does not interfer with the ability of the receptors to bind the toxins. Preferably, latex beads or the wells of plastic microtiter plates are used. The latter are preferably used in the RELISA of the invention.

As used herein, a receptor is a chemical that binds to an SLT. Preferably, the receptors are represented by the formula X—O—Y(R):

wherein Y is sphingosine, hydroxylated sphingosine, or saturated sphingosine;

wherein X is a carbohydrate moiety selected from the group consisting of-Gal(alpha1-4)Gal, Gal(alpha1-4)Gal(beta1-4)Glc, GalNAc(beta1-3)Gal(alpha1-4)Gal(beta1-4)Glc, GalNAc(beta1-3)Gal(alpha1-4)Gal, GalNAc(beta1-3)Gal, and GalNAc; and wherein R is H or a chemical group non-inhibitory to receptor binding, preferably a fatty acid, and R is linked to the amine moiety of the sphingosine.

Most preferably, the receptors are the deacyleted form of $Gb_3$. It is most preferably bound to the well of a microtiter plate for use in an ELISA for the detection of SLT. The receptor-bound toxin is visualized by the use of the antibodies of the invention and an immunoperoxidase indicator system. Other such systems well-known to those skilled in the art would also be suitable.

Because there are over 50 serotypes of verotoxin-producing *E. coli*, any satisfactory overall diagnostic strategy must be directed toward detecting the verotoxin rather than the organism. The receptor ELISA of the invention is 100% specific and can detect 0.1 picograms of SLT/ml. This is as sensitive or more sensitive than the standard cytotoxicity assay and far superior to standard antibody capture ELISAs. Using the receptor-ELISA, screening fecal filtrates for the toxin is a straightforward procedure and test results can be obtained in as little as 10 minutes, compared with cytotoxicity testing which routinely requires 2–5 days to receive results from the Center for Disease Control.

The IgG or antibodies of the invention may also be used in the biochemical, immunological, functional, or other investigational analysis of SLTs and SLT-producing microorganisms. Thus, the invention provides improved methods and compositions for such scientific analysis. An effective amount of the IgG or antibodies for providing the information desired in such analysis, preferably in an acceptable carrier, is used. Determination of the amount necessary to accomplish a particular research goal depends upon the specific type of investigation involved, and it is readily within the skill of one carrying out such research, given the teachings contained herein.

Thus, the invention also comprises reagents and kits for detecting the presence of SLTs, which would have utility in scientific research, clinical diagnosis, and food safety procedures.

In one embodiment, the reagent comprises the purified IgG or the purified antibodies of the invention in a liquid that does not affect the activity of the antibodies in the intended assay. Preferably, the liquid is saline solution. Alternatively, the reagent comprises the purified IgG or purified antibodies attached to a substrate as discussed above. Preferably, the substrate is an insoluble solid support, most preferably the well of a microtiter plate. An alternative preferred substrate is solid particles, most preferably latex beads.

The diagnostic kit comprises, in a container, one or more of the reagents of the invention and a means for detecting or measuring the formation of complexes created by the binding of the toxins and the antibodies in the reagents. The antibodies may be attached to the walls of the container that are exposed to the sample. Preferably, the insoluble substrate is the well of a microtiter plate.

The detecting or measuring means is preferably an immunoassay, such radioimmunoassay, enzyme-linked immunosorbent assay (ELISA), and immunofluorescence assay. Most preferably, the detecting or measuring means is a reagent capable of binding to the complexes formed by the SLT and the antibodies and containing a detectable moiety. Such reagent may be the antibody of the invention conjugated with a detectable moiety or an SLT receptor conjugated to a detectable moiety. Alternatively, the antibody can be a second antibody, which is an antibody to the antibodies of the invention, conjugated to a detectable moiety. An example of such a second antibody is goat anti-IgG labelled with peroxidase.

Most preferably, the diagnostic kit contains an SLT receptor attached to a solid support and the purified IgG or antibodies of the invention. Preferably the solid support is the well of a microtiter plate. Preferably, the kit further contains means for detecting the binding of the anti-SLT antibodies in the purified IgG to SLT bound to the receptor. This means is preferably one of the assays discussed above. Most preferably, it is one or more reagents capable of detecting the receptor-SLT-antibody complexes discussed above.

It is to be understood that application of the teachings of the present invention to a specific problem or environment will be within the capabilities of one having ordinary skill in the art in light of the teachings contained herein. Examples of the products of the present invention, process for its production, and process for its use appear in the following examples.

EXAMPLE I

Preparation of Shiga-Like Toxins SLT-II and SLT-IIv For Inoculation of Preparturient Cows Crude toxins were first prepared as follows. Two-liter cultures of *E. coli* DH5 transformed with recombinant plasmids containing cloned toxin genes were grown for 24 to 48 h with shaking at 37° C. in LB with 250 micrograms of ampicillin per ml. Maniatis et al., *Molecular Cloning: A Laboratory Manual*, (Cold Spring Harbor Laboratory, Cold Spring Harbor, N.Y.) (1982). The cells were pelleted by centrifugation, washed, and suspended in 50 ml of LB. Next, the pelleted cells were disrupted by sonication, and the sonic extract was clarified by centrifugation at 12,000× g for 15 min. The toxin was then precipitated from the clarified sonic extract with 60% saturated ammonium sulfate by centrifugation at 17,000×g for 30 min. The resultant pellet was suspended in 25 ml of PBS and dialyzed against PBS overnight. This material served as crude toxin stock.

Purified SLT-II and SLT-IIv were generated from these crude materials by the following method. Crude SLT-II was bound to a DEAE-Sepharose column that had been equilibrated with 50 mM Tris (pH 7.0). Fractions were eluted with a 0 to 1.0M NaCl-50 mM Tris hydrochloride (pH 7.0) gradient, and each fraction was assayed for Vero cytotoxicity. The fractions that contained the highest cytotoxic activities were pooled, dialyzed, and then passed over a chromatofocusing column as described in O'Brien et al., *Infec. Immun.* 40:675–683 (1983). Fractions with the highest cytotoxic activities were pooled, dialyzed and separated by antitoxin affinity chromatography according to Downes et al., *Infect. Immun.* 56:1926–1933 (1988). Monoclonal antibody BC5BB12 (a kind gift of Nancy Strockbrine) served as the immunoabsorbent. Bound toxin was eluted with 50 mM glycine (pH 2.8) and immediately neutralized with 1M Tris hydrochloride (pH 7.5). The affinity step was repeated, and the cytotoxic fractions were pooled, dialyzed against PBS, and stored at 4° C.

SLT-IIv was purified by a similar protocol with the following modifications. Ion-exchange chromatography was performed with CM-Sepharose rather than DEAE-Sepharose, because the predicted pI for SLT-IIvp is <9.0. The CM-Sepharose column was equilibrated with 50 mM sodium phosphate (pH 8.0), and toxin was eluted by using a 0 to 1.0M NaCl-50 mM sodium phosphate (pH 8.0) gradient. The pH range used in the chromatofocusing column was 8 to 10.5 (Polybuffer exchanger 118 and Pharmalyte 8–10.5; Pharmacia, Inc.).

The purity of both toxin preparations was assessed by sodium dodecyl sulfate-polyacrylamide gel electrophoresis under reducing conditions, and each appeared as three bands representing toxin subunits A, $A_1$, and B. Laemmli, *Nature* (London) 227:680–685 (1970). Proteins on the gels were visualized either by silver stain (Rapid-Ag-stain; ICN Biomedicals Inc., Lisle, Ill.) or by autoradiography of iodinated toxin. Hunter et al., *Nature* (London) 194:495–496 (1962). The protein concentrations of samples were determined by Bio-Rad Protein Assay reagents (Bio-Rad Laboratories, Richmond, Calif.).

EXAMPLE II

Inoculation of Pregnant Cows With SLT For Antibody Production

Heffers were procurred approximately 3 months prior to term of first pregnancy. Three separate cows were injected with purified toxin, one with each major antigenic class of toxin (SLT-I, SLT-II, or SLT-IIv). Four inoculations with 1 mg of purified protein per challenge via intramuscular injection were performed. The timing of each inoculation was as follows: 28 days between first and second inoculation and 14 days between subsequent challenges. Pre-challenge and post-challenge sera were collected to monitor antibody response to toxin. After each cow delivered, four milkings were collected at 8 hour intervals. After milkings, the animal was sacrificed and sera was collected.

EXAMPLE III

Preparation of Purified Immunoglobulin from Milk

IgG was purified from whole colostrum/milk according to the method of Boesman-Finkelstein et al., *Infect. Immun.* 57:1227–1234 (1989). Whole colostrum/milk was heated to 39°–40° C. to liquefy the fat. Cream was then removed using a centrifuge separator. Rennin (2 mg/ml) was added to the resultant skim milk, and the pH was lowered to 6 with HCl. After 1–2 h at 30° C. to set the casein clot, a clear yellowish whey was obtained by centrifugation at 9000×g for 15 min. The immunoglobulin was precipitated from the whey at 35% saturation of ammonium sulfate at 4° C. overnight. The soluble immunoglobulin was extensively dialyzed against phosphate buffered saline, and the IgG was separated by protein A sepharose affinity column. Antibody was passed over a protein A column and unbound protein was eluted with saline. Bound antibody was eluted with 100 mM glycine, pH 2.8 and dialyzed against saline. Typically, >15% of the total protein passed over the protein A column was IgG.

EXAMPLE IV

Preparation of Purified Immunoglobulin from Serum

Serum from immunized cows was used to isolate IgG with high specific anti-toxin activity as follows: Protein was precipitated from serum by the addition of 35% ammonium sulfate at 4° C. and centrifugation at 10,000×g for 30 minutes. The protein pellet was resuspended in saline and passaged over a protein A column to isolate IgG as described in Example III.

EXAMPLE V

Evaluation of Purified IgG

Purified IgG was evaluated for protein concentration using a MicroBCA assay (RioRad Inc., Sunnyvale, Calif.) Purified IgG was evaluated for homogeneity by SDS-PAGE and staining by both silver and coomassie blue. The purity of the IgG was shown by the fact that it produced only two bands on the gels. The bands were at about 47 kDa and 30 kDa, which represented the heavy and light chains of the IgG.

The level of antitoxin-specific antibody was determined by several methods. The ability to neutralize the cytotoxic effect of toxin for Vero cells was measured as described by Samuel et al., Infect. Immun. 58:611–618 (1990). Ten-fold serial dilutions of antisera or purified antibody were incubated with 20 Vero $CD_{50}$ of toxin for 1 h at 37° C. This mixture was then added to $10^4$ Vero cells that were seeded in 96-well microtiter wells. The cells were incubated for 48 h and then stained with crystal violet for determination of toxin mediated cell death. The ability of each dilution to neutralize the effect of toxin was measured visually. The average neutralizing titers were 1:250,000/mg IgG. The level of toxin-reactive antibody was measured by ELISA, and the average titers were 1:12,000/mg IgG. The ELISA was performed by first coating a 96 well microtiter plate with toxin (1 ug/well). Serial dilutions of antibody were incubated in the toxin-coated wells for 1 hours, washed with saline, and anti-bovine HRP-conjugated antisera was then incubated for 30 minutes. The ELISA was developed with TMB substrate (Biorad Inc.).

The monospecificity of each antibody for toxin occurring in a mixed culture sonicate was evaluated by Western blot. A bacterial culture of *E. coli* which produce the toxin was grown to stationary phase, pelleted, and resuspended in SDS-PAGE sample buffer. This material was separated on a 12% SDS-PAGE gel, then transfered to nitrocellulose. The nitrocellulose was first incubated with PBS containing 3% geletin, then incubated with PBS containing 15 geletin and 10 microgram/ml of antibody. Reactive antibody was subsequently detected with anti-bovine antibody conjugated with horseradish peroxidase and detected by standard ELISA. The toxin A and B subunits were the only major immunoreactive proteins when 10 microgram/ml of IgG was used.

The efficacy of each antibody in the receptor-based ELISA (RELISA) was demonstrated and 1 microgram/test well generated an optimum signal to noise detection ratio. These antibodies generated an enhanced signal compared with previously characterized monoclonal antibodies.

EXAMPLE VI

Preparation of High Titer, Monospecific, Purified Polyclonal Antibodies to an SLT Antibody that is specific for Shiga-like toxin was purified from isolated IgG that was separated from other serum components according to Example IV. The procedures disclosed in Carlton, *Methods in Enzymology* (Jakoby, W. B., Ed.), vol. 104:381–387, Academic Press, New York (1984) and Porath, et al., *Nature* (London) 215:1491–1492 (1967) were applied as follows. Toxin-specific antibody was isolated using a cyanogen bromide-activated sepharose 4B column (Pharmacia, Inc.) onto which purified SLT was bound to serve as an immunoabsorbent for toxin-specific antibodies. Sepharose beads were prepared for coupling to toxin by first swelling in 1 mM HCl and then washing in coupling buffer (100 mM $NaHCO_3$, 500 mM NaCl , pH 8.3) Purified SLT was first dialyzed against coupling buffer, then mixed with the beads at room temperature for 2 h. The bead and toxin mixture was washed with 100 mM Tris, pH 8.0, and then reacted with this buffer at room temperature for 2 h to quench the coupling reaction. The beads were washed exhaustively, alternating between coupling buffer and acetate buffer (100 mM sodium acetate, 500 mM NaCl, pH 4.0). These beads then were used to prepare a column for antibody purification. Protein A purified IgG was first dialyzed against phosphate buffered saline (PBS, 10 mM sodium phosphate, 167 mM NaCl, pH 7.4), then loaded on the toxin affinity column. Non-reactive antibody was removed by equilibration with PBS, and toxin-specific antibody was removed by elution with 100 mM glycine, pH 2.8. The avidity of an individual antibody elution was controlled by changing the salt concentration in the equilibration buffer to select antibody with different ranges of avidity. Eluted IgG was dialyzed against PBS containing 0.1% sodium azide and stored at −80° C.

EXAMPLE VII

Latex Agglutination Assay

A 2.5% suspension of latex particles (Polysciences Inc., 0.98 m) in glycine-buffered saline, pH 8.2, was mixed with an equal volume of anti-SLT-II bovine polyclonal IgG1 antibodies to give a final concentration of antitoxin of 0.8 mg/ml. The latex beads were incubated for 1 hour at 37° C. in a water bath with occasional shaking.

The sensitized latex beads were then centrifuged for 3 min. at 4,000 r.p.m., washed once with saline and suspended in glycine-buffered saline, pH 8.2, containing 0.1% bovine serum albumin and 0.02% sodium azide. The latex beads were next incubated an additional 30 min. at 37° C. Control latex particles were sensitized with normal bovine globulin in the same manner as anti-verotoxin-adsorbed particles. The sensitized latex particles were stored at 4° C. before use.

An equal volume (25 microliters) of latex bead suspension was mixed with an equal volume of sample to be tested on a dark glass plate or slide. After mixing well with an applicator stick, the plate was placed on an orbital shaker for 3–5 min. Clumping of the beads indicated a positive agglutination reaction, showing the presence of SLT-II in the clinical sample.

EXAMPLE VIII

Receptor ELISA Assay

The polyclonal, monospecific bovine antibody was used to enhance the signal generated in a receptor-based ELISA (RELISA) over monoclonal antibodies using the following protocol. The RELISA plate was prepared by using the receptor analogue lyso-$Gb_3$ to coat wells of a 96-well microtiter plate at 1 microgram of lyso-$Gb_3$/well. The plates were then blocked with 1% gelatin in saline solution, rinsed with saline solution, and incubated with primary antibody at 37° C. for 90 minutes. The wells were then washed and incubated with secondary antibody which was enzymatically labeled with horseradish peroxidase for 60 minutes. The wells were then washed, and TMB substate (Biorad Inc) was used to develop the assay. The superior efficiency of detection of bound toxin by the polyclonal monospecific bovine antibody versus mouse monoclonal antitoxin antibody is shown in FIG. 1. Toxin was detected at greater than 10-fold higher sensitivity using the bovine sera as compared to the toxin-specific antibody 11E10.

It will be apparent to those skilled in the art that various modifications can be made to processes and products of the present invention. Thus, it is intended that the present invention covers the modifications and variations of this invention provided they come within the scope of the appended claims and their equivalents.

We claim:

1. Purified IgG, comprising high titer, monospecific polyclonal antibodies to Shiga-like toxin (SLT) obtained by a process comprising the steps of:

inoculating a bovine animal with a purified, active SLT, derived from *E. coli* and selected from the group consisting of SLT I, SLT II, SLT IIV and mixtures thereof; and recovering and purifying IgG from said animal after said animal has had an immune response to said purified active SLT.

2. A method for producing high titer, monospecific, polyclonal antibodies to Shiga-like toxin (SLT) comprising the steps of:

inoculating a bovine animal with a purified, active SLT, derived from *E. coli* and selected from the group consisting of SLT I, SLT II, SLT IIV and mixtures thereof; and recovering and purifying IgG from said animal after said animal has had an immune response to said purified active SLT.

3. The method of claim 2 wherein said animal is a pregnant cow.

4. The method of claim 3 for producing the purified polyclonal antibodies further comprising:

milking said inoculated bovine animal after said animal has had an immune response to said purified SLT to obtain colostrum or milk.

5. The method of claim 2 for producing the purified polyclonal antibodies further comprising the step of:

recovering the purified polyclonal antibodies by affinity chromatography using purified SLT bound to a chromatographic support.

6. A reagent for use in an assay for the detection of an SLT in a sample comprising the purified antibody produced by the method of claim 2 in a liquid.

7. A reagent for use in an assay for the detection of an SLT in a sample comprising the purified antibody produced by the method of claim 2 attached to a substrate.

8. The reagent of claim 7 wherein said substrate is an insoluble solid support.

9. The reagent of claim 8 wherein said solid support is the well of a microtiter plate.

10. The reagent of claim 8 wherein said solid support is a latex bead.

11. A method for detecting the presence of an SLT or SLT-producing bacteria in a sample comprising the steps of:

contacting said sample with the purified IgG of claim 1; and determining if an antibody-antigen reaction has occurred.

12. The method of claim 11 wherein said IgG is attached to a soluble or insoluble substrate.

13. The method of claim 11 wherein said IgG is attached to a solid support and said step of determining if an antibody-antigen reaction has occurred comprises the steps of:

contacting IgG-SLT complexes formed if said antibody-antigen reaction has occurred with a second antibody to said SLT, wherein said other antibody is labeled with a detectable moiety, thereby forming IgG-SLT-second antibody complexes;

removing unbound second antibody; and detecting the presence of said detectable moiety.

14. The method of claim 13 wherein said IgG is bound to solid particles and the presence of said SLT is detected by the agglutination of said solid particles.

15. The method of claim 11 wherein said IgG is attached to latex beads and said step of determining if an antibody-antigen reaction has occurred comprises visually determining if said latex beads in said sample have agglutinated.

16. A method for detecting the presence or concentration of an SLT in a sample comprising the steps of using said sample in an immunoassay wherein the purified IgG of claim 1 is used as a reagent in said immunoassay.

17. A method for the passive immunization of a human or animal against SLT toxemia comprising administering to said human or animal a prophylactically effective amount of the purified IgG of claim 1 to prevent said toxemia.

18. A method for the treatment of SLT toxemia in a human or animal comprising administering a therapeutically effective amount of the purified IgG of claim 1 to treat said toxemia to said human or animal.

* * * * *